United States Patent
Hynes et al.

(10) Patent No.: US 9,744,289 B2
(45) Date of Patent: Aug. 29, 2017

(54) METHOD TO DETERMINE CONTRAST MEDIA INJECTION PARAMETERS TO CONTROL SIGNAL INTENSITY DURING MAGNETIC RESONANCE ANGIOGRAPHY

(75) Inventors: Michael R. Hynes, Chesterfield, MO (US); Dennis A. Moore, Ferguson, MO (US); William J. Neubert, Manchester, MO (US)

(73) Assignee: LIEBEL-FLARSHEIM COMPANY LLC, Cincinnati, OH (US)

( * ) Notice: Subject to any disclaimer, the term of this patent is extended or adjusted under 35 U.S.C. 154(b) by 741 days.

(21) Appl. No.: 14/003,893

(22) PCT Filed: Mar. 14, 2012

(86) PCT No.: PCT/US2012/029038
§ 371 (c)(1),
(2), (4) Date: Sep. 9, 2013

(87) PCT Pub. No.: WO2012/129022
PCT Pub. Date: Sep. 27, 2012

(65) Prior Publication Data
US 2013/0345548 A1     Dec. 26, 2013

Related U.S. Application Data

(60) Provisional application No. 61/453,975, filed on Mar. 18, 2011.

(51) Int. Cl.
| | | |
|---|---|---|
| A61B 5/055 | (2006.01) | |
| A61M 5/00 | (2006.01) | |
| A61M 5/145 | (2006.01) | |

(52) U.S. Cl.
CPC ............. *A61M 5/007* (2013.01); *A61B 5/055* (2013.01); *A61M 5/1452* (2013.01); *A61M 5/14546* (2013.01)

(58) Field of Classification Search
CPC ..... A61B 5/055; A61M 5/007; A61M 5/1452; A61M 5/14546
See application file for complete search history.

(56) References Cited

U.S. PATENT DOCUMENTS

| | | |
|---|---|---|
| 5,806,519 A | 9/1998 | Evans, III et al. |
| 5,840,026 A | 11/1998 | Uber, III et al. |
| | (Continued) | |

FOREIGN PATENT DOCUMENTS

| | | |
|---|---|---|
| EP | 1647291 | 4/2006 |
| WO | 00/61216 | 10/2000 |
| | (Continued) | |

*Primary Examiner* — Ruth S Smith
(74) *Attorney, Agent, or Firm* — Marsh Fischmann & Breyfogle LLP

(57) ABSTRACT

Injection systems and related methods including an injection device, an operator interface, and modules to determine operational parameters during an MRA imaging procedure. Such parameters may be used to optimize and/or maximize signal intensity during an MRA imaging procedure. The injection system may include a target in-bloodstream contrast agent concentration determination module that determines a target in-bloodstream contrast agent concentration at least partially based on contrast agent type and MRA imager parameters. The injection system may include a contrast agent injection rate determination module that determines a contrast agent injection rate at least partially based on the target in-bloodstream contrast agent concentration, an initial contrast agent concentration, and a cardiac output rate of a patient to be imaged. The injection system may include a diluent injection rate determination module that determines a diluent injection rate at least partially based on the contrast agent injection rate.

15 Claims, 8 Drawing Sheets

(56) References Cited

U.S. PATENT DOCUMENTS

| | | |
|---|---|---|
| 6,470,889 B1 | 10/2002 | Bae et al. |
| 6,635,030 B1 | 10/2003 | Bae et al. |
| 6,889,072 B2 | 5/2005 | Prince |
| 6,928,338 B1 | 8/2005 | Buchser et al. |
| 6,970,735 B2 | 11/2005 | Uber, III et al. |
| 2006/0215815 A1* | 9/2006 | Rasche .................. A61B 6/481 378/95 |
| 2007/0282198 A1 | 12/2007 | Uber, III et al. |

FOREIGN PATENT DOCUMENTS

| | | |
|---|---|---|
| WO | 00/64353 | 11/2000 |
| WO | 2007116840 A1 | 10/2007 |
| WO | 2008/085421 | 7/2008 |
| WO | 2008/137375 | 11/2008 |
| WO | 2009/012023 A1 | 1/2009 |

\* cited by examiner

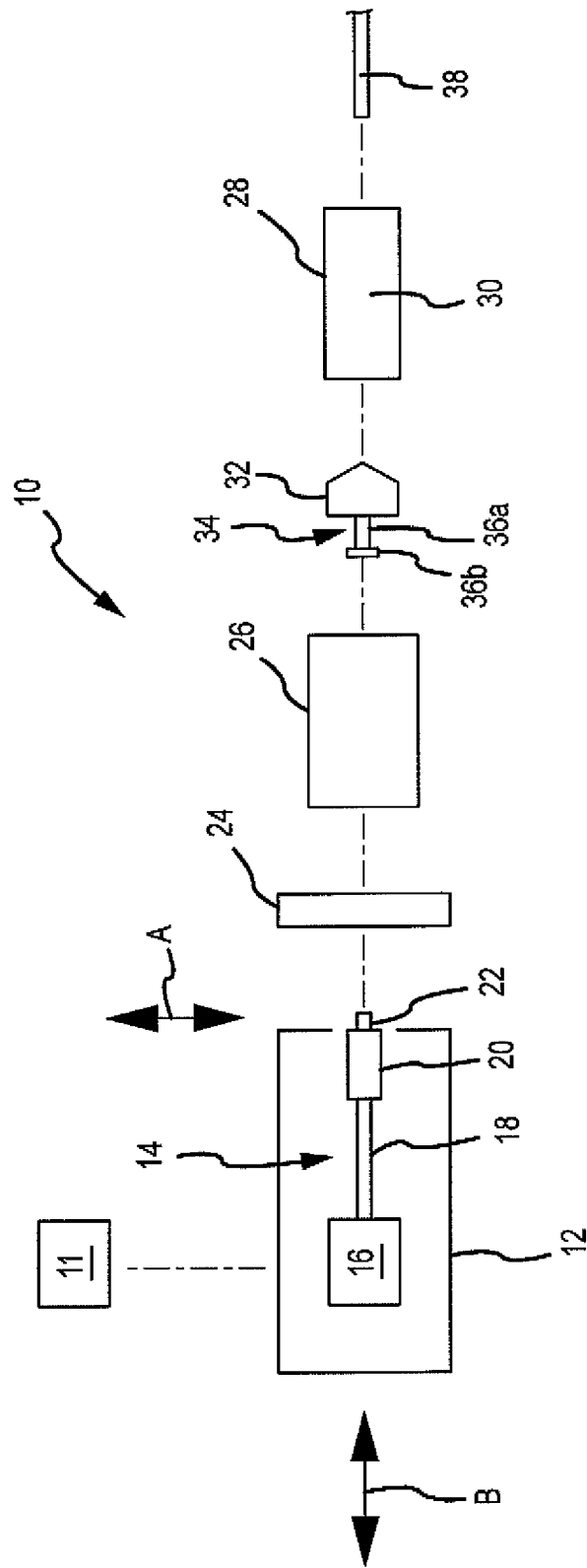

METHOD TO DETERMINE CONTRAST MEDIA INJECTION PARAMETERS TO CONTROL SIGNAL INTENSITY DURING MAGNETIC RESONANCE ANGIOGRAPHY

RELATED APPLICATIONS

This application claims priority to U.S. provisional application Ser. No. 61/453,975 filed on 18 Mar. 2011 and entitled "APPARATUS AND METHOD TO DETERMINE CONTRAST MEDIA INJECTION PARAMETERS TO CONTROL SIGNAL INTENSITY DURING MAGNETIC RESONANCE ANGIOGRAPHY".

FIELD OF THE INVENTION

The present invention generally relates to the field of magnetic resonance angiography (MRA) and, more particularly, to the field of contrast media injection and resultant signal intensity during an MRA imaging procedure.

BACKGROUND

Various medical procedures require that one or more medical fluids be injected into a patient. For example, medical imaging procedures oftentimes involve the injection of contrast media into a patient, possibly along with saline and/or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

Power injectors may be used to deliver contrast media (or also commonly referred to as a "contrast agent") during MRA imaging procedures. The contrast agent is used to enhance the imagery generated by the MRA imager. Test injections are performed on a patient and subsequent delivery rates of contrast agent are based on the results of the test injections. Contrast agent delivery may be followed by a saline push.

SUMMARY

A first aspect of the present invention is provided by a method of operation for an injection system in relation to an MRA imaging procedure utilizing an MRA imager. The method includes inputting into the injection system: a type of contrast agent; an initial contrast agent concentration for the type of contrast agent; a cardiac output rate for a patient to be imaged; and a first imaging parameter. The method further includes the injection system determining a target in-bloodstream contrast agent concentration and a contrast agent injection rate. The target in-bloodstream contrast agent concentration determination is at least partially based on the type of contrast agent and the first imaging parameter. The contrast agent injection rate calculation is at least partially based on the target in-bloodstream contrast agent concentration, the initial contrast agent concentration, and the cardiac output rate. The contrast agent injection rate is calculated to achieve the target in-bloodstream contrast agent concentration. The method further includes operating the injection system in accordance with the calculated contrast agent injection rate.

A number of feature refinements and additional features are applicable to the first aspect of the present invention. These feature refinements and additional features may be used individually or in any combination. As such, each of the following features that will be discussed may be, but are not required to be, used with any other feature or combination of features of the first aspect. The following discussion is applicable to the first aspect, up to the start of the discussion of a second aspect of the present invention.

The method may include the injection system retrieving attributes of the type of contrast agent from a database stored in the injection system. The determination of the target in-bloodstream contrast agent concentration may be at least partially based on the retrieved attributes of the type of contrast agent. In this regard, the database may include attributes associated with a plurality of types of contrast agents. The determination of the target in-bloodstream contrast agent concentration may include using a formula relating contrast agent concentration in the patient to signal intensity received by the MRA imager during the MRA imaging procedure to determine a first level of concentration of the contrast agent, where the rate at which the signal intensity changes divided by the rate at which the contrast agent concentration changes equals zero. In an embodiment, the target in-bloodstream contrast agent concentration may be equal to the first level of concentration.

A second imaging parameter may be inputted into the injection system. In an embodiment, the first imaging parameter may be a pulse repetition time for the MRA imager, and the second imaging parameter may be an imaging delay time for the MRA imager. The target in-bloodstream contrast agent concentration determination may be further based on the second imaging parameter.

The calculation of the contrast agent injection rate may include dividing the target in-bloodstream contrast agent concentration by the initial contrast agent concentration to determine a concentration ratio, and calculating the contrast agent injection rate by multiplying the cardiac output rate by the concentration ratio.

The method may also include calculating a diluent injection rate at least partially based on the contrast agent injection rate. The calculation of the diluent injection rate may include selecting a standard total injection rate, and subtracting the contrast agent injection rate from the standard fluid injection rate to determine the diluent injection rate. This standard total injection rate may be in the form of a default value for the injection system, or may be input to the injection system in any appropriate manner (e.g., through an operator/graphical user interface). The value for the standard total injection rate may be acquired or determined in any appropriate manner (e.g., empirically).

The operation of the injection system may include injecting the patient with the type of contrast agent that was input and at the contrast agent injection rate that was calculated by the injection system. In embodiments of the method that include injecting the patient with diluent at the diluent injection rate, the injection of diluent may occur simultaneously with the injection of the contrast agent (e.g., into a single injection site on a patient, for instance where the contrast agent and diluent discharges merge into a common conduit).

A second aspect of the present invention is provided by an injection system that includes an injection device, an operator interface, a target in-bloodstream contrast agent concentration determination module, and a contrast agent injection rate determination module. The operator interface may allow an operator to provide various inputs to the injection system. The target in-bloodstream contrast agent concentration determination module determines a target in-bloodstream contrast agent concentration at least partially based on a contrast agent type input (e.g., input via the operator interface) and a first imaging parameter for an MRA imager to be used in an MRA imaging procedure. The contrast agent injection rate determination module determines a contrast agent injection rate at least partially based on the target in-bloodstream contrast agent concentration, an initial contrast agent concentration input, and a cardiac output rate input of a patient to be imaged.

A number of feature refinements and additional features are applicable to the second aspect of the present invention. These feature refinements and additional features may be used individually or in any combination. As such, each of the following features that will be discussed may be, but are not required to be, used with any other feature or combination of features of the second aspect. The following discussion is applicable to the second aspect, up to the start of the discussion of a third aspect of the present invention.

One or more of the contrast agent type input, the initial contrast agent concentration input, the cardiac output rate input, and the first imaging parameter may be entered or input into the injection system through the operator interface. The target in-bloodstream contrast agent concentration determination module may further utilize a second imaging parameter. The first imaging parameter may be a pulse repetition time for the MRA imager, while the second imaging parameter may be an imaging delay time for the MRA imager.

The target in-bloodstream contrast agent concentration determination module may use a formula relating contrast agent concentration in the patient to signal intensity received by the MRA imager during the MRA imaging procedure. In this regard, the target in-bloodstream contrast agent concentration determination module may determine a first level of concentration of the contrast agent, where the rate at which the signal intensity changes divided by the rate at which the contrast agent concentration changes equals zero. The target in-bloodstream contrast agent concentration may be equal to the first level of concentration.

The contrast agent injection rate determination module may function by dividing the target in-bloodstream contrast agent concentration by the initial contrast agent concentration input to determine a concentration ratio, and calculating the contrast agent injection rate by multiplying the cardiac output rate by the concentration ratio.

The injection system may further include a diluent injection rate determination module that determines a diluent injection rate at least partially based on the contrast agent injection rate. The diluent injection rate determination module may subtract the contrast agent injection rate from a standard total injection rate to determine the diluent injection rate.

A third aspect of the present invention is provided by a method of operation for an injection system in relation to an MRA imaging procedure utilizing an MRA imager. The injection system includes a syringe with a contrast agent. The method includes selecting a formula relating contrast agent concentration in a patient to be imaged to signal intensity received by the MRA imager during the MRA imaging operation. The method further includes obtaining a first imaging parameter for use in the MRA imaging procedure, and determining, using at least the formula and the first imaging parameter, an in-bloodstream contrast agent concentration of the contrast agent, where the rate at which the signal intensity changes divided by the rate at which the in-bloodstream contrast agent concentration changes equals zero. The method further includes discharging the contrast agent from the syringe at a contrast agent injection rate based on the in-bloodstream contrast agent concentration.

A number of feature refinements and additional features are applicable to the third aspect of the present invention. These feature refinements and additional features may be used individually or in any combination. As such, each of the following features that will be discussed may be, but are not required to be, used with any other feature or combination of features of the third aspect. The following discussion is applicable to the third aspect, up to the start of the discussion of a fourth aspect of the present invention.

The first imaging parameter may be obtained by transferring the first imaging parameter from the MRA imager to the injection system via a communicative link of any appropriate type. The first imaging parameter may also be obtained by a user entering the first imaging parameter into the injection system through a graphical user interface of the injection system (or via any appropriate data input device). The method may further include obtaining a second imaging parameter for use in the MRA imaging procedure. In such a method, the first imaging parameter may be a pulse repetition time for the MRA imager, and the second imaging parameter may be an imaging delay time for the MRA imager. The determination of the in-bloodstream contrast agent concentration of the contrast agent may be further based upon the second imaging parameter.

The formula selection may be performed by the injection system based on an imaging sequence to be used by the MRA imager. The determination of the in-bloodstream contrast agent concentration of the contrast agent may be performed by the injection system.

The method may further include inputting a cardiac output rate for the patient, determining a target in-bloodstream contrast agent concentration based on the in-bloodstream contrast agent concentration, dividing the target in-bloodstream contrast agent concentration by a concentration of the contrast agent in the syringe to determine a concentration ratio, and calculating the contrast agent injection rate by multiplying the cardiac output rate by the concentration ratio. In such an embodiment, the target in-bloodstream contrast agent concentration may be equal to the in-bloodstream contrast agent concentration.

The method may further include acquiring a standard total injection rate, subtracting the contrast agent injection rate from the standard total injection rate to determine a first diluent injection rate, and discharging diluent at the first diluent injection rate simultaneously with the discharging of the contrast agent. Both the diluent and contrast agent may be directed to a common injection site on a patient.

A fourth aspect of the present invention is provided by an injection system including an injection device, a syringe installed on the injection system and holding or containing a contrast agent, an operator interface that may allow an operator to provide various inputs to the injection system, a memory, and a target in-bloodstream contrast agent concentration determination module. The memory may include a plurality of formulas, and each of the plurality of formulas may relate contrast agent concentration in a patient to be imaged by an MRA imager to signal intensity received by the MRA imager during an MRA imaging procedure for a particular imaging sequence type. The target in-bloodstream contrast agent concentration determination module may determine a target in-bloodstream contrast agent concentration using at least a first imaging parameter of the MRA imager and one of the plurality of formulas. The target in-bloodstream contrast agent concentration determination module may determine an in-bloodstream contrast agent concentration of the contrast agent, where the rate at which the signal intensity changes divided by the rate at which the in-bloodstream contrast agent concentration changes equals zero.

A number of feature refinements and additional features are applicable to the fourth aspect of the present invention. These feature refinements and additional features may be used individually or in any combination. As such, each of the following features that will be discussed may be, but are not required to be, used with any other feature or combination of features of the fourth aspect. The following discussion is applicable to the fourth aspect, up to the start of the discussion of a fifth aspect of the present invention.

Individual formulas of the plurality of formulas may be related to a spin-echo imaging sequence, a gradient-echo imaging sequence, or any other appropriate imaging sequence.

The target in-bloodstream contrast agent concentration determination module may further use a second imaging parameter of the MRA imager to determine the in-bloodstream contrast agent concentration. For example, the first imaging parameter may be a pulse repetition time for the MRA imager, and the second imaging parameter may be an imaging delay time for the MRA imager.

The injection system may further include a contrast agent injection rate determination module that determines a contrast agent injection rate at least partially based on the in-bloodstream contrast agent concentration. The contrast agent injection rate determination module may determine the contrast agent injection rate at least partially based on an initial contrast agent concentration of the contrast agent in the syringe and a cardiac output of a patient to be imaged. The contrast agent injection rate determination module may divide the target in-bloodstream contrast agent concentration by the initial contrast agent concentration to determine a concentration ratio. The contrast agent injection rate determination module may then multiply the cardiac output rate input by the concentration ratio to determine the contrast agent injection rate.

The injection system may further include a diluent injection rate determination module that determines a diluent injection rate at least partially based on the contrast agent injection rate. The diluent injection rate determination module may subtract the contrast agent injection rate from a standard total injection rate to determine the diluent injection rate.

A fifth aspect of the present invention is provided by a method of operation of an injection system, which includes a syringe with a contrast agent, in relation to an MRA imaging procedure utilizing an MRA imager. The method includes inputting a cardiac output rate for a patient to be imaged, calculating a concentration ratio by dividing a target in-bloodstream contrast agent concentration by a concentration of the contrast agent in the syringe, determining a contrast agent injection rate by multiplying the cardiac output rate by the concentration ratio, and discharging the contrast agent from the syringe at the contrast agent injection rate. The discharge may be initiated only after the contrast agent injection rate has been determined. In an embodiment, the method may further include subtracting the contrast agent injection rate from a standard total injection rate to determine a first diluent injection rate, and discharging diluent at the first diluent injection rate simultaneously with the discharging of the contrast agent (e.g., to a common injection site on a patient).

A sixth aspect of the present invention is provided by an injection system that includes an injection device, a syringe installed on the injection system and holding a contrast agent, an operator interface that may allow an operator to provide various inputs to the injection system, and a contrast agent injection rate determination module. The contrast agent injection rate determination module determines a contrast agent injection rate by multiplying a cardiac output rate of a patient to be imaged by a ratio of a target in-bloodstream contrast agent concentration to a concentration of the contrast agent in the syringe.

A number of feature refinements and additional features are applicable to the sixth aspect of the present invention. These feature refinements and additional features may be used individually or in any combination. As such, each of the following features that will be discussed may be, but are not required to be, used with any other feature or combination of features of the sixth aspect. The following discussion is applicable to the sixth aspect, up to the start of the discussion of a seventh aspect of the present invention.

The injection system may further include a diluent injection rate determination module that determines a diluent injection rate at least partially based on the contrast agent injection rate. The diluent injection rate determination module may subtract the contrast agent injection rate from a standard total injection rate to determine the diluent injection rate.

A seventh aspect of the present invention is provided by a method of operation of an injection system in relation to an MRA imaging procedure utilizing an MRA imager. The method includes determining a first contrast agent injection rate of a first type of contrast agent to a first patient to be imaged for a first MRA imaging procedure, and subtracting the first contrast agent injection rate from a standard fluid injection rate to determine a first diluent injection rate. The method further includes simultaneously discharging from the injection system the first type of contrast agent at the first contrast agent injection rate and discharging diluent at the first diluent injection rate (e.g., to a common injection site on a patient).

A number of feature refinements and additional features are applicable to the seventh aspect of the present invention. These feature refinements and additional features may be used individually or in any combination. As such, each of the following features that will be discussed may be, but are not required to be, used with any other feature or combination of features of the seventh aspect. The following discussion is applicable to the seventh aspect, up to the start of the discussion of an eighth aspect of the present invention.

The method may further include determining a second contrast agent injection rate of a second type of contrast agent to a second patient to be imaged for a second MRA imaging procedure, subtracting the second contrast agent injection rate from the standard fluid injection rate to determine a second diluent injection rate, and simultaneously discharging from the injection system the second type of contrast agent at the second contrast agent injection rate and discharging diluent at the second diluent injection rate (e.g., to a common injection site on a patient). The first contrast agent injection rate may be different than the second contrast agent injection rate. The first type of contrast agent may be of a different type of contrast agent than the second type of contrast agent.

The simultaneous discharge from the injection system of the first type of contrast agent at the first contrast agent injection rate and of diluent at the first diluent injection rate may be performed by a dual-head power injector of the injection system.

An eighth aspect of the present invention is provided by an injection system that includes a dual-head power injector with a first syringe installed on the dual-head power injector and holding or containing a contrast agent, and a second syringe installed on the dual-head power injector and holding or containing diluent. The injection system further includes an operator interface that allows an operator to provide various inputs to the injection system, and a diluent injection rate determination module that determines a diluent injection rate by subtracting a contrast agent injection rate from a standard total injection rate. The injection system further includes a controller that causes the dual-head power injector to simultaneously discharge the contrast agent from the first syringe at the contrast injection rate and diluent from the second syringe at the diluent injection rate (e.g., to a common injection site on a patient).

A number of feature refinements and additional features are separately applicable to each of above-noted first, second, third, fourth, fifth, sixth, seventh and eighth aspects of the present invention. These feature refinements and additional features may be used individually or in any combination in relation to each of the above-noted first, second, third, fourth, fifth, sixth, seventh and eight aspects. Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a power injector includes "a syringe" alone does not mean that the power injector includes only a single syringe). Moreover, any failure to use phrases such as "at least one" also does not limit the corresponding feature to the singular (e.g., indicating that a power injector includes "a syringe" alone does not mean that the power injector includes only a single syringe). Use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical). Finally, a reference of a feature in conjunction with the phrase "in one embodiment" does not limit the use of the feature to a single embodiment.

Any "determination module" that may be utilized by any of the various aspects of the present invention may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. This determination module may be implemented at any single location or at multiple locations that are interconnected in any appropriate manner (e.g., via any type of network).

Any power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading and/or drawing of fluid and/or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

Any such power injector may be used for any appropriate application where the delivery of one or more medical fluids is desired, including without limitation any appropriate medical imaging application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging) and/or any appropriate medical diagnostic and/or therapeutic application (e.g., injection of chemotherapy, pain management, etc.). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with any such power injector in any appropriate manner (e.g., detachably; front-loaded; rear-loaded; side-loaded), any appropriate medical fluid may be discharged from a given syringe of any such power injector (e.g., contrast media, therapeutic fluid, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., medical tubing set), where this conduit is fluidly interconnected with the syringe in any appropriate manner and directs fluid to a desired location (e.g., to a catheter that is inserted into a patient for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injectors syringe plunger drive assembly such that the syringe plunger drive assembly is able to advance the plunger in at least one direction, and possibly in two different, opposite directions.

As used herein, the term "fluidly interconnected" refers to two or more components or entities being connected (directly or indirectly) in a manner such that fluid can flow (e.g., unidirectionally or bidirectionally) in a predetermined flow path therebetween. For example, "an injection device fluidly interconnected to a patient" describes a configuration where fluid can flow from the injection device through any interconnecting devices (e.g., tubing, connectors) and into the patient (e.g., into the vasculature of the patient).

BRIEF DESCRIPTION OF THE FIGURES

FIG. 1 is a schematic of one embodiment of a power injector.

DETAILED DESCRIPTION

Figure 2A:
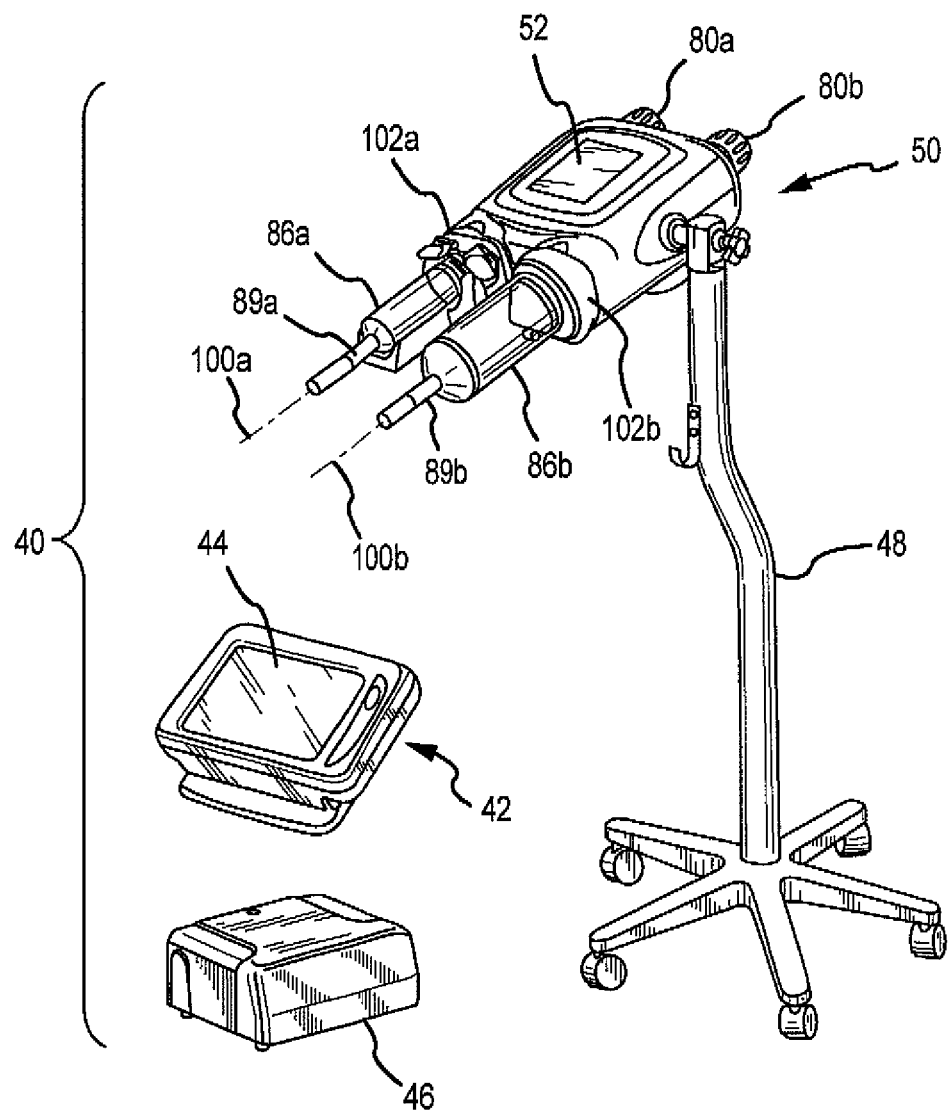
FIG. 2A is a perspective view of one embodiment of a portable stand-mounted, dual-head power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide any of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on the powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, these components may or may not be coupled when the ram 20 advances the syringe plunger 32 to discharge fluid from the syringe 28 (e.g., the ram 20 may simply "push on" the syringe plunger coupler 34 or directly on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. Two syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
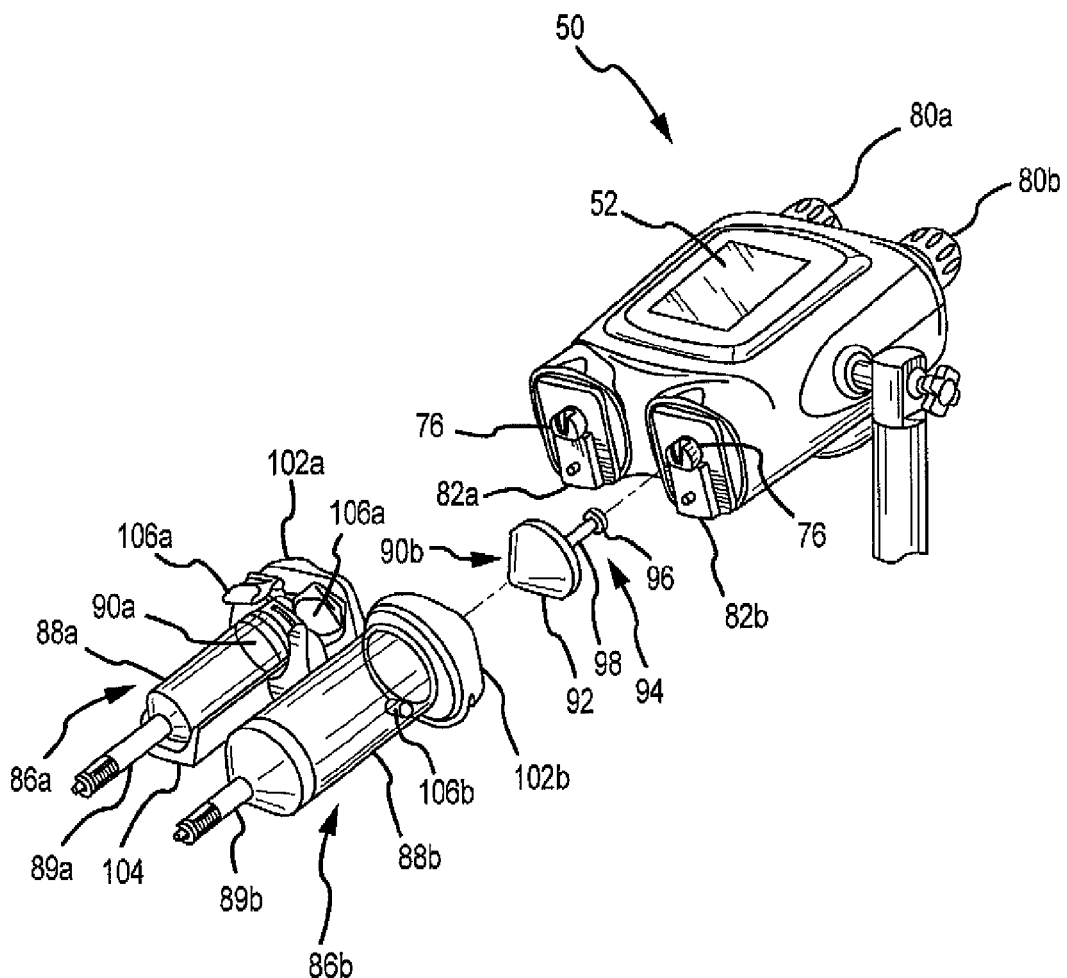
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88*a* through a nozzle 89*a* of the syringe 86*a*. An appropriate conduit (not shown) will typically be fluidly interconnected with the nozzle 89*a* in any appropriate manner to direct fluid to a desired location (e.g., a patient). Similarly, the syringe 86*b* includes plunger or piston 90*b* that is movably disposed within a syringe barrel 88*b*. Movement of the plunger 90*b* along an axis 100*b* (FIG. 2A) via operation of the powerhead 50 will discharge fluid from within the syringe barrel 88*b* through a nozzle 89*b* of the syringe 86*b*. An appropriate conduit (not shown) will typically be fluidly interconnected with the nozzle 89*b* in any appropriate manner to direct fluid to a desired location (e.g., a patient).

The syringe 86*a* is interconnected with the powerhead 50 via an intermediate faceplate 102*a*. This faceplate 102*a* includes a cradle 104 that supports at least part of the syringe barrel 88*a*, and which may provide/accommodate any additional functionality or combination of functionalities. A mounting 82*a* is disposed on and is fixed relative to the powerhead 50 for interfacing with the faceplate 102*a*. A ram coupler 76 of a ram 74 (FIG. 2C), which are each part of a syringe plunger drive assembly or syringe plunger driver 56 (FIG. 2O) for the syringe 86*a*, is positioned in proximity to the faceplate 102*a* when mounted on the powerhead 50. Details regarding the syringe plunger drive assembly 56 will be discussed in more detail below in relation to FIG. 2C. Generally, the ram coupler 76 may be coupled with the syringe plunger 90*a* of the syringe 86*a*, and the ram coupler 76 and ram 74 (FIG. 2C) may then be moved relative to the powerhead 50 to move the syringe plunger 90*a* along the axis 100*a* (FIG. 2A). It may be such that the ram coupler 76 is engaged with, but not actually coupled to, the syringe plunger 90*a* when moving the syringe plunger 90*a* to discharge fluid through the nozzle 89*a* of the syringe 86*a*.

The faceplate 102*a* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*a* on and remove the faceplate 102*a* from its mounting 82*a* on the powerhead 50. The faceplate 102*a* may be used to couple the syringe plunger 90*a* with its corresponding ram coupler 76 on the powerhead 50. In this regard, the faceplate 102*a* includes a pair of handles 106*a*. Generally and with the syringe 86*a* being initially positioned within the faceplate 102*a*, the handles 106*a* may be moved to in turn move/translate the syringe 86*a* at least generally within a plane that is orthogonal to the axes 100*a*, 100*b* (associated with movement of the syringe plungers 90*a*, 90*b*, respectively, and illustrated in FIG. 2A). Moving the handles 106*a* to one position moves/translates the syringe 86*a* (relative to the faceplate 102*a*) in an at least generally downward direction to couple its syringe plunger 90*a* with its corresponding ram coupler 76. Moving the handles 106*a* to another position moves/translates the syringe 86*a* (relative to the faceplate 102*a*) in an at least generally upward direction to uncouple its syringe plunger 90*a* from its corresponding ram coupler 76.

The syringe 86*b* is interconnected with the powerhead 50 via an intermediate faceplate 102*b*. A mounting 82*b* is disposed on and is fixed relative to the powerhead 50 for interfacing with the faceplate 102*b*. A ram coupler 76 of a ram 74 (FIG. 2C), which are each part of a syringe plunger drive assembly 56 for the syringe 86*b*, is positioned in proximity to the faceplate 102*b* when mounted to the powerhead 50. Details regarding the syringe plunger drive assembly 56 again will be discussed in more detail below in relation to FIG. 2C. Generally, the ram coupler 76 may be coupled with the syringe plunger 90*b* of the syringe 86*b*, and the ram coupler 76 and ram 74 (FIG. 2C) may be moved relative to the powerhead 50 to move the syringe plunger 90*b* along the axis 100*b* (FIG. 2A). It may be such that the ram coupler 76 is engaged with, but not actually coupled to, the syringe plunger 90*b* when moving the syringe plunger 90*b* to discharge fluid through the nozzle 89*b* of the syringe 86*b*.

The faceplate 102*b* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*b* on and remove the faceplate 102*b* from its mounting 82*b* on the powerhead 50. The faceplate 102*b* also may be used to couple the syringe plunger 90*b* with its corresponding ram coupler 76 on the powerhead 50. In this regard, the faceplate 102*b* may include a handle 106*b*. Generally and with the syringe 86*b* being initially positioned within the faceplate 102*b*, the syringe 86*b* may be rotated along its long axis 100*b* (FIG. 2A) and relative to the faceplate 102*b*. This rotation may be realized by moving the handle 106*b*, by grasping and turning the syringe 86*b*, or both. In any case, this rotation moves/translates both the syringe 86*b* and the faceplate 102*b* at least generally within a plane that is orthogonal to the axes 100*a*, 100*b* (associated with movement of the syringe plungers 90*a*, 90*b*, respectively, and illustrated in FIG. 2A). Rotating the syringe 86*b* in one direction moves/translates the syringe 86*b* and faceplate 102*b* in an at least generally downward direction to couple the syringe plunger 90*b* with its corresponding ram coupler 76. Rotating the syringe 86*b* in the opposite direction moves/translates the syringe 86*b* and faceplate 102*b* in an at least generally upward direction to uncouple its syringe plunger 90*b* from its corresponding ram coupler 76.

As illustrated in FIG. 2B, the syringe plunger 90*b* includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90*b* and its corresponding ram coupler 76 are in a coupled state or condition. The syringe plunger 90*a* may include a similar syringe plunger coupler 94 for interfacing with its corresponding ram coupler 76.

Figure 2C:
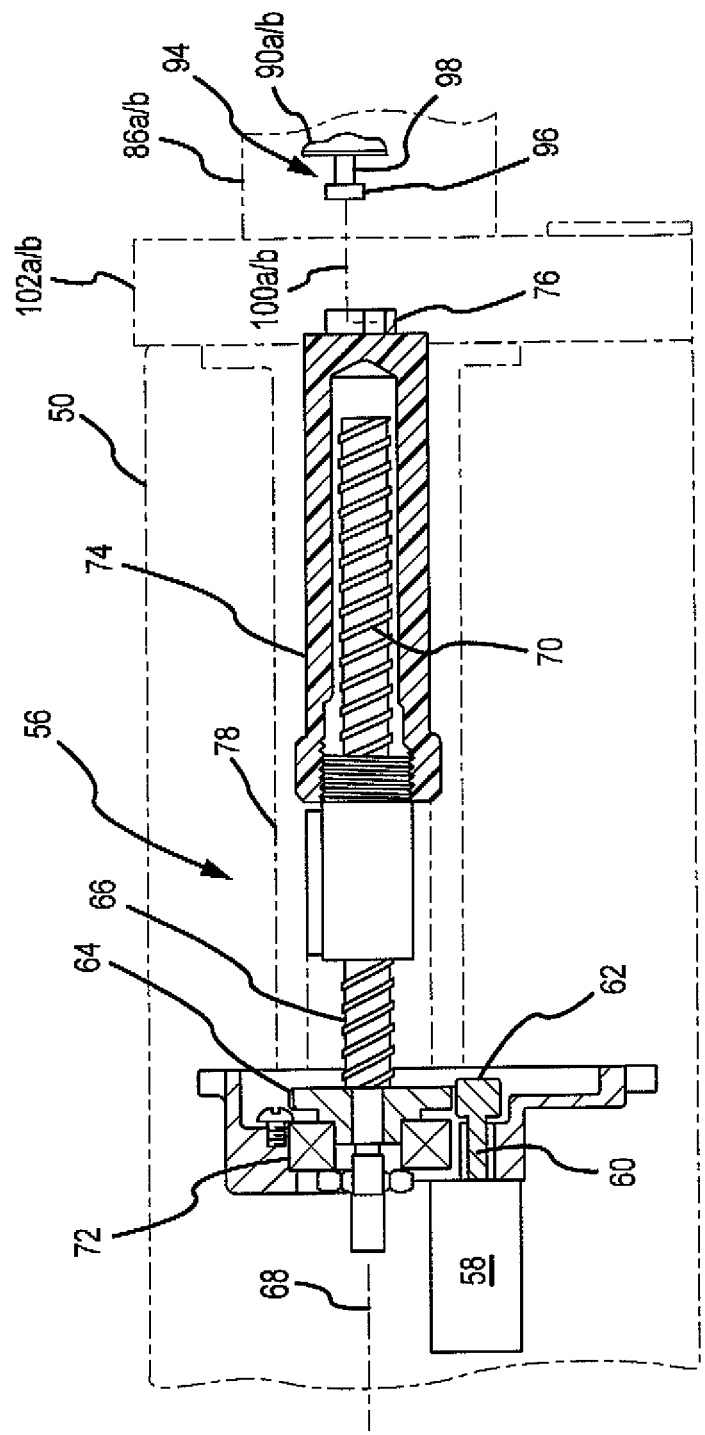
FIG. 2C is a schematic of one embodiment of a syringe plunger drive assembly used by the power injector of FIG. 2A.

The powerhead 50 is utilized to discharge fluid from the syringes 86*a*, 86*b* in the case of the power injector 40. That is, the powerhead 50 provides the motive force to discharge fluid from each of the syringes 86*a*, 86*b*. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86*a*, 86*b*. A separate syringe plunger drive assembly 56 may be incorporated into the powerhead 50 for each of the syringes 86*a*, 86*b*. In this regard and referring back to FIGS. 2A-B, the powerhead 50 may include hand-operated knobs 80*a* and 80*b* for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 2C illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86a/b may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient) and/or any appropriate medical diagnostic and/or therapeutic application (e.g., injection of chemotherapy, pain management, etc.). Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other component's. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, therapeutic fluid, a radiopharmaceutical, a diluent, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

The power injectors 10, 40 and injection systems described herein may be used in conjunction with magnetic resonance imaging equipment to perform an MRA imaging procedure. Such imaging equipment is referred to herein as an MRA imager. The MRA imaging procedure may be used to image blood vessels to evaluate their condition, for example to look for narrowing, vessel wall dilations, aneurysms or any other appropriate condition. The injection systems may be used to deliver contrast agent to a patient to enhance images generated by the MRA imager.

At a given MRA imager magnetic field strength, the contrast agents decrease the longitudinal and transverse relaxation times ($T_1$ and $T_2$, respectively) according to the relationships:

$$\frac{1}{T_1} = \frac{1}{T_{10}} + r_1[M] \quad (1)$$

$$\frac{1}{T_2} = \frac{1}{T_{20}} + r_2[M] \quad (2)$$

where: $T_1$=observed longitudinal relaxation time; $T_{10}$=longitudinal relaxation of the substance without any contrast agent; $r_1$=longitudinal relaxivity; $T_2$=observed transverse relaxation time; $T_{20}$=transverse relaxation of the substance without any contrast agent; $r_2$=transverse relaxivity; and [M]=concentration of contrast agent.

Figure 3:
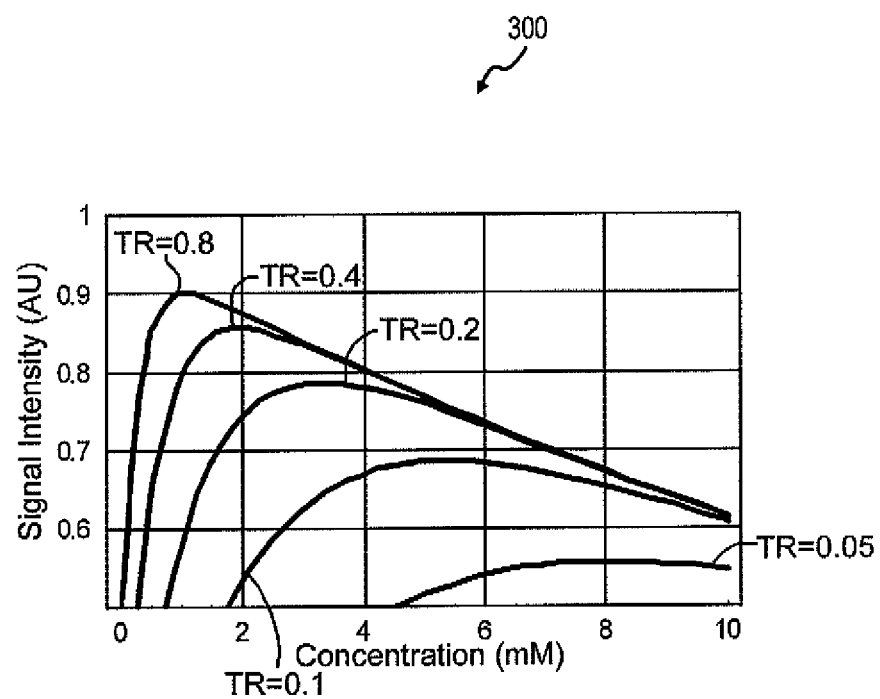
FIG. 3 is a graph of signal intensity versus concentration for various pulse repetition times for a representative contrast agent.

The above relationships may be used in conjunction with formulas relating signal intensity (SI) with MRA imager parameters. For example, in the case of an MRA imager using a spin-echo imaging sequence, the following formula may be used:

$$SI = (1 - e^{-TR/T_1})e^{-TE/T_2} \quad (3)$$

where TR=pulse repetition time and TE=imaging delay time. The above equations may be used to generate the graph 300 of FIG. 3, which illustrates the relationship between concentration (millimolar (mM)) for MAGNEVIST® contrast agent (available from Bayer HealthCare Pharmaceuticals Inc., Wayne, N.J.) and signal intensity (arbitrary units (AU)) for various pulse repetition times (with TE=10 milliseconds (ms), magnetic field strength=1.5 Tesla (T)).

A concentration ($M_{opt}$) where the signal intensity is at a maximum for a given pulse repetition time can be found where a peak of the curve has zero slope with respect to concentration:

$$\frac{d(SI)}{d[M]} = 0 \Rightarrow [M_{opt}] = T_{10}\text{Ln}\left(1 + \left(\frac{r_1}{r_2}\right)\left(\frac{TR}{TE}\right)\right) - \frac{1}{r_1 T_{10}} \quad (4)$$

In this regard, the particular concentration that corresponds to a maximum signal intensity may be determined. Accordingly, maximum signal intensity and its corresponding concentration level may be determined for any particular set of the above variables (e.g., for any particular combination of contrast agent attribute(s), pulse repetition time, and imaging delay time).

Figure 4:
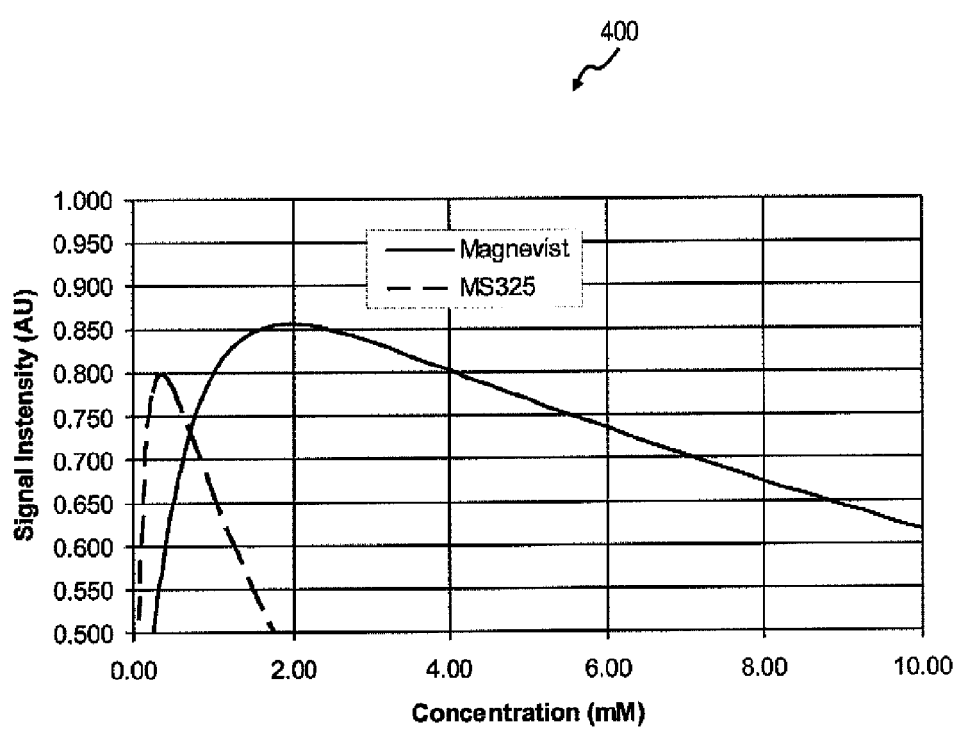
FIG. 4 is a graph of signal intensity versus concentration for two representative contrast agents.

As illustrated in graph 400 of FIG. 4, different types of contrast agent may produce different concentration versus signal intensity profiles. The graph of 400 illustrates curves for MAGNEVIST® and MS325 (also known as VASOVIST®, available from Epix Pharmaceuticals, Inc., Lexington, Mass.) where the magnetic field strength equals 1.51, TR=400 ms, and TE=10 ms. It will be appreciated that a particular contrast agent concentration level (e.g., about 2 mM) may yield a satisfactory signal intensity for one type of contrast agent (e.g., a signal intensity of about 0.850 AU for MAGNEVIST®) while yielding undesirable results for another type of contrast agent (e.g., a signal intensity of less than 0.500 AU for MS325).

Similarly, a concentration may be chosen to reduce the effects of concentration variation. For example, in the graph 300 of FIG. 3, along the curve labeled TR=0.8, if a concentration level is selected to correspond to the maximum signal intensity, the subsequent signal intensity during the imaging procedure may be particularly sensitive to a concentration level below the target. This is due to the steep drop-off of signal intensity along the curve labeled TR=0.8 to the left of its maximum point. In such situations, it may be desirable to choose a selected target concentration level that does not correspond to a maximum point. For example, a user (e.g., clinician, doctor) may select a target concentration level that is slightly greater than the concentration level that corresponds to the maximum point to reduce the sensitivity of the resultant signal intensity to variations in the concentration level.

The above equations and the related discussion relate to spin-echo imaging sequences. Other imaging sequences, such as gradient echo imaging sequences, may be treated similarly.

As illustrated in the graph 400 of FIG. 4, the magnitudes of concentrations that correspond to maximum signal intensity may be relatively low as compared to typical contrast agent formulated concentrations (e.g., as supplied by a supplier). Typical contrast agent formulated concentrations may be higher than the concentrations required for imaging. For example, MS325 and MAGNEVIST® may come in concentrations of 200 mM and 500 mM, respectively. Accordingly, a significant dilution is required in order to achieve concentration levels in the blood that correspond to a desired signal intensity. Too much dilution or too little dilution may lead to significant decreases in the resulting signal intensity.

In order to obtain a precise dilution in blood to achieve the target in-bloodstream contrast agent concentration, the injection rate at which the contrast agent is injected into the patient may be linked with the patients cardiac output (expressed in milliliters/second (mL/sec)) as described in the following equation:

$$CAIR = CO \frac{TC}{SC} \quad (5)$$

where: TC=target concentration (mM); CO=cardiac output (ml/sec); SC=starting concentration of contrast agent (mM); and CAIR=contrast agent injection rate (mL/sec). For example, a patient with a cardiac output of 83 mL/sec undergoing an MRA imaging procedure using MAGNEVIST® with a starting concentration of 500 mM, and where the target concentration was calculated to be 1.96 mM (using the formulas described above), may require a contrast agent injection rate of (1.96 mM/500 mM)×83 mL/sec 0.33 mL/sec. The contrast agent may be injected into a vein at the calculated contrast agent injection rate to achieve the desired target concentration in the bloodstream exiting the heart. Generally, contrast agents that are supplied in such relatively high concentration levels may result in contrast agent injection rates that are as low as or lower than the example given above. Additionally, patients with a lower cardiac output may require even lower contrast agent rejection rates.

However, such relatively low contrast agent injection rates may significantly decrease control over the concentration and the timing of the contrast agent bolus. In this regard, and using the example above, a contrast agent injection rate of 0.33 ml/sec into a vein (e.g., in an arm) of a patient may not result in a uniform 0.33 ml/sec of contrast agent delivered to the heart of the patient. Additionally, such low injection rates may result in undesirable time between when the injection is performed and when the contrast agent reaches the heart of the patient. To produce a more consistent, predictable and timely flow of contrast agent to the heart of the patient through the vein, the contrast agent may be diluted on the fly (e.g., just prior to entering the bloodstream of the patient) to inject a more diluted solution at a faster rate. In this regard, a total injection rate (TIR) may be selected to increase the controllability, predictability and/or speed at which the contrast agent moves to the heart of the patient, and the contrast agent may be diluted on the fly to achieve the total injection rate. In this regard, the injection device may simultaneously inject contrast agent and an appropriate diluent (e.g., saline) to achieve the total injection rate. The injection rate of the diluent may be calculated by subtracting the contrast agent injection rate from the total injection rate using the formula: DIR=TIR−CAIR, where DIR=diluent injection rate.

Furthermore, the total injection rate may be a standard rate that could be applied to multiple patients independent of the desired contrast agent injection rate and patient cardiac output. In one embodiment, a total injection rate may be on the order of 2 to 3 mL/sec. For example, a user may select a total injection rate of 2 mL/sec. Applying such a total injection rate to the above example, a diluent injection rate of 2 mL/sec−0.33 mL/sec=1.67 mL/sec may be calculated. Accordingly, the contrast agent and diluent may be simultaneously injected into a patient at 0.33 mL/sec and 1.67 mL/sec, respectively, to achieve a total injection rate of 2 mL/sec. Such a method may provide for greater control over the movement of the contrast agent to the heart as compared to known methods such as administering the contrast agent followed by a saline push.

Figure 5:
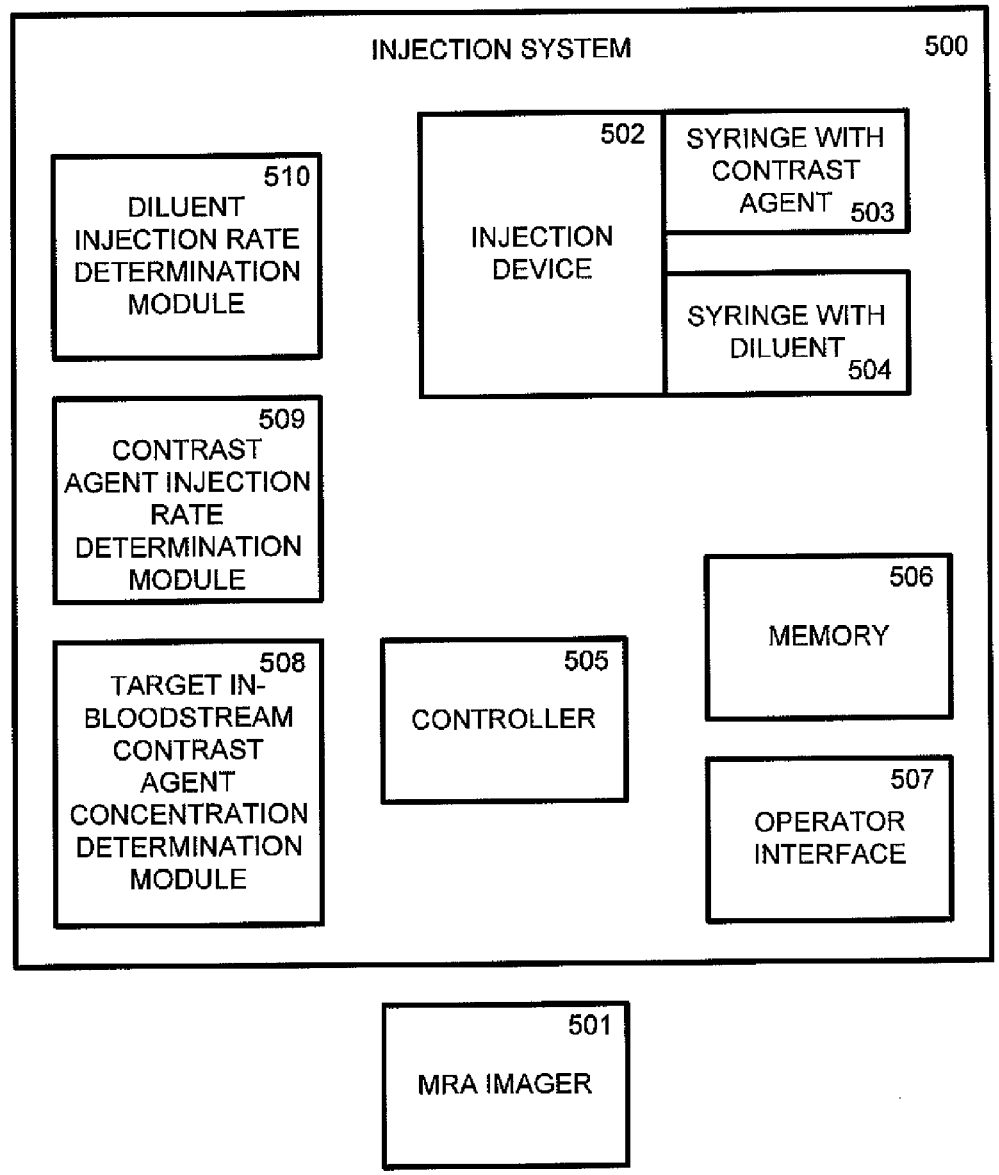
FIG. 5 is a block diagram of an injection system and an MRA imager.

FIG. 5 is a block diagram of an injection system 500 and an MRA imager 501. The injection system 500 may include an injection device 502. The injection device 502 may be in the form of the power injectors 10, 40 discussed above. For example, the injection device 502 may be a dual-head power injector. A syringe containing contrast agent (hereafter "contrast agent syringe") 503 and a syringe containing diluent (hereafter "diluent syringe") 504 may be installed on the injection device 502. The injection device 502 may be operable to simultaneously and independently control the injection of contrast agent from the contrast agent syringe 503 and the injection of diluent from the diluent syringe 504.

Both the contrast agent syringe 503 and the diluent syringe 504 may be fluidly interconnected to a fluid outlet (not shown), such as a single catheter that may be disposed in a patient. Both the contrast agent syringe 503 and the diluent syringe 504 may be fluidly interconnected to a mixing device (not shown, and optional) to mix the contrast agent and diluent before reaching the catheter.

The injection system 500 may further include a controller 505 operatively interconnected to the injection device 502. The controller 505 may interact with various other internal components of the injection system 500 along with various external devices and/or systems, such as the MRA imager 501 and/or a computer network. The controller 505 may be a separate component or it may be distributed among the various components of the injection system 500. The controller 505 may interact with the injection device 502 to control the injection rates from the contrast agent syringe 503 and/or the diluent syringe 504.

The injection system 500 may further include a memory 506. The memory 506 may store a plurality of formulas and related information (e.g., in a database). Each of the plurality of formulas may relate contrast agent concentration in a patient to be imaged by the MRA imager 501 to signal intensity received by the MRA imager 501 during an MRA imaging procedure for a particular imaging sequence type (e.g., spin-echo, gradient echo). The memory 506 may further store attributes of a plurality of different types of contrast agents (e.g., $r_1$ and $r_2$ used in equations (1) and (2)). Injection system 500 and subsystem software may also be stored in the memory 506 along with any other appropriate software, data, protocols, or instructions.

An operator interface 507 may be included with the injection system 500. The operator interface 507 may be operable to receive inputs from an operator of the injection system 500 and to produce outputs (e.g., visual outputs on a display, audio outputs) for the operator. The operator interface 507 may include a GUI. The operator interface 507 may include a touchscreen, a display and keyboard, or any other appropriate device or combination of devices. The operator interface 507 may be operatively interconnected to the controller 505. In this regard, the controller 505 may receive inputs from the user and may provide output for the user through the operator interface 507.

The injection system 500 may further include a target in-bloodstream contrast agent concentration determination module (hereinafter "target determination module") 508. The target determination module 508 may determine a target in-bloodstream contrast agent concentration at least partially based on the contrast agent type to be used and at least one imaging parameter to be used by the MRA imager 501 during an MRA imaging procedure. For example, for a particular MRA imaging procedure utilizing a spin-echo imaging sequence, it may be desirable to use a contrast agent concentration that yields maximum signal intensity. In such a case, the target determination module 508 may use equation (4) above to determine the concentration ($M_{opt}$) which would equal the target in-bloodstream contrast agent concentration. The operator may indicate the type of contrast agent to be used in the MRA imaging procedure through the operator interface 507. Alternatively, the type of contrast agent may be obtained by the injection system when the contrast agent syringe 503 is installed on the injection device 502 (e.g., by reading a barcode on the syringe 503). Values for $r_1$ and $r_2$ that are associated with the type of contrast agent may be retrieved from the memory 506 by the controller 505. Furthermore, the operator may, using the operator interface 507, indicate values for TR and TE to be used by the MRA imager 501. Alternatively, the MRA imager 501 may be in communication with the controller 505 of the injection system 500 and TR and TE may be obtained by the controller 505 through such communication (e.g., direct communication link, network communication link). $T_{10}$ may be provided by the operator or a value for $T_{10}$ may be retrieved from the memory 506. Using such values, the target determination module 508 may then determine the target in-bloodstream contrast agent concentration and forward the concentration to the controller 505. It is noted that the values for $r_1$, $r_2$, $T_{10}$ and $T_{20}$ are field strength dependent. Accordingly, the operator may enter the field strength of the MRA imager 501 into the operator interface 507.

The injection system 500 may further include a contrast agent injection rate determination module 509. The contrast agent injection rate determination module 509 may determine a contrast agent injection rate at least partially based on the target in-bloodstream contrast agent concentration (TC) (e.g., obtained as described above), the starting concentration of contrast agent (SC), and the cardiac output (CO) of the patient to be imaged. For example, the contrast agent injection rate determination module 509 may use equation (5) in making such a determination. The value for target in-bloodstream contrast agent concentration may be obtained from the target determination module 508 (e.g., through the controller 505). The value for the starting concentration may be manually entered into the operator interface 507 or it may be obtained by the injection system when the contrast agent syringe 503 is installed on the injection device 502 (e.g., by reading a barcode on the syringe 503). The value for cardiac output of the patient may be entered by the operator through the operator interface 507. The value for cardiac output may be determined using any appropriate method, including through medical testing of the patient and/or estimation based on various attributes of the patient (e.g., age, blood pressure, weight).

The injection system 500 may further include a diluent injection rate determination module 510. The diluent injection rate determination module 510 may determine a diluent injection rate (DIR) at least partially based on the contrast agent injection rate (CAIR) (e.g., obtained as described above) and the total injection rate (TIR). For example, the diluent agent injection rate determination module 510 may use the formula: DIR=TIR−CAIR as described above in making such a determination. The value for contrast agent injection rate may be obtained from the contrast agent injection rate determination module 509 (e.g., through the controller 505). The value for the total injection rate may be manually entered into the operator interface 507 or a standard value for the total injection rate may be obtained from the memory 506.

The injection system 500 in combination with the MRA imager 501 may be used to optimize the signal intensity from the vasculature (e.g., arteries) during an MRA imaging procedure. Such optimization may encompass selecting a contrast agent concentration level to maximize signal intensity. Such optimization may be based on factors including, but not limited to, the patient (cardiac output), contrast agent (concentration, relaxivities), the MRA imager 501 (field strength), and MRA imager 501 settings (pulse repetition time, imaging delay time). As a system, the operational parameters of the injection system 500 in combination with the MRA imager 501 may be selected to achieve specific goals. For example, parameters may be selected to obtain the maximum possible MRA signal intensity from vasculature with the least possible dose of contrast agent. In another example, parameters may be selected to maximize the MRA imager's 501 "imaging window", or time after injection over which a clinically useful enhanced image can be acquired. Other considerations may include increasing MRA imager 501 throughput (e.g., reducing scan times) by reducing pulse repetition time or balancing MRA imager 501 throughput and contrast agent usage to achieve cost-efficient operation of the injection system 500 in combination with the MRA imager 501.

In summary, the injection system 500 in combination with the MRA image 501 described herein may be operable to achieve specific operational goals (e.g., maximum MRA imager signal intensity with the least possible dose of contrast agent) by taking into account and/or controlling all of or at least some of the following parameters: contrast agent type and initial concentration, contrast agent longitudinal and transverse relaxation times, target in-bloodstream contrast agent concentration, contrast agent injection rate, diluent injection rate, total injection rate, type of MRA imager pulse sequence, MRA imager signal intensity, MRA imager field strength, MRA imager pulse repetition time, MRA imager imaging delay time, and patient cardiac output.

Figure 6:
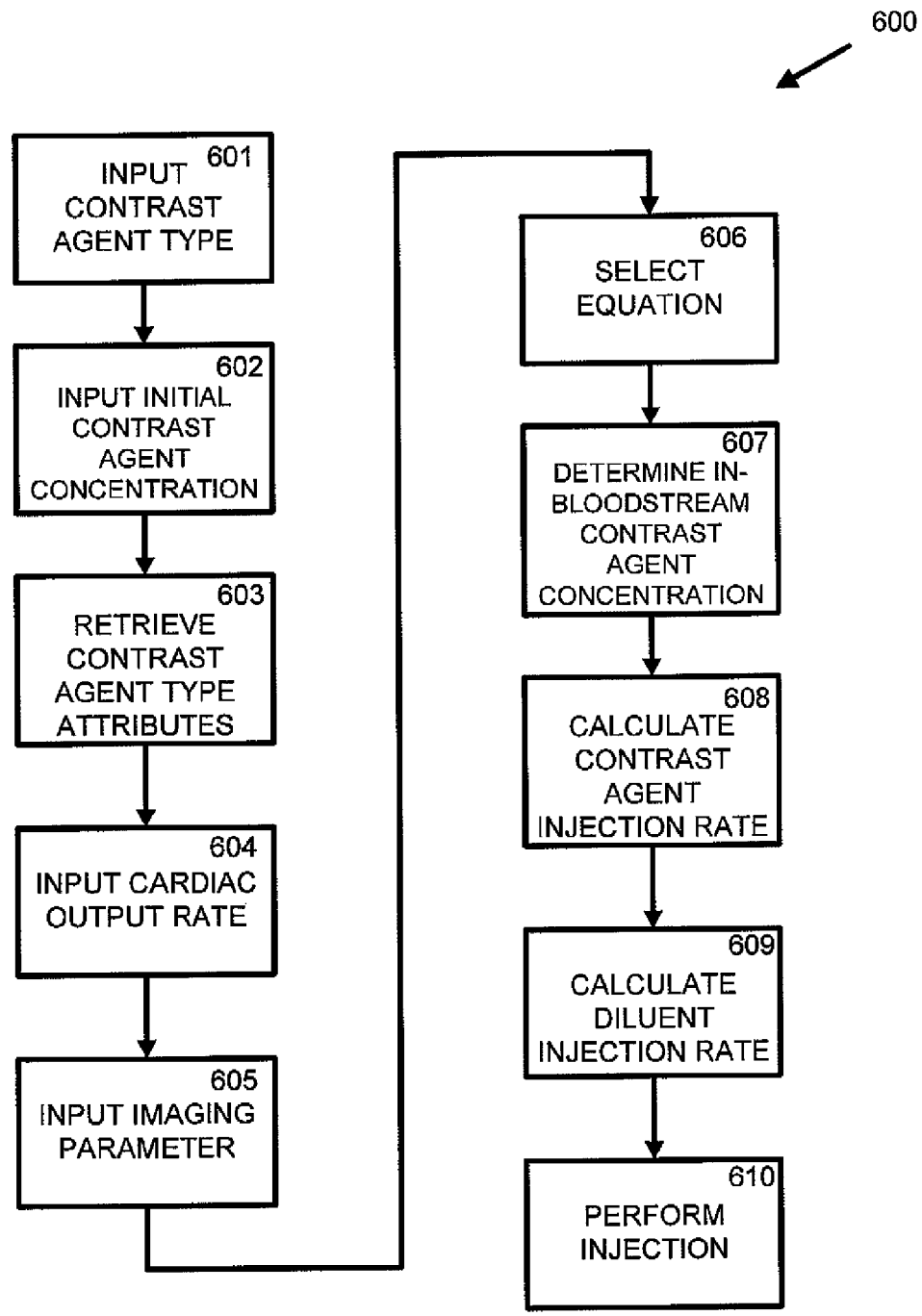
FIG. 6 is a flow diagram of a method of operating an injection system in relation to an MRA imager.

FIG. 6 is a flow diagram 600 of a method operating an injection system in relation to an MRA imaging procedure. The method will be described with reference to the injection system 500 and MRA imager 501 of FIG. 5. A first step 601 may to input the contrast agent type to be used during the MRA imaging procedure. The next step 602 may be to input the initial contrast agent concentration. Steps 601 and 602 may be performed by the operator through the operator interface 507 (e.g., a GUI) or, for example, the steps may be performed by a barcode reader associated with the injection system 500 reading a barcode associated with the contrast agent (e.g., on the contrast agent syringe 503). In another example, steps 601 and 602 may be performed by an electromagnetic communication device associated with the injection system 500 reading a radio frequency identification (RFID) tag associated with the contrast agent syringe 503. Alternatively, the injection system 500 may assume a default type and/or concentration of contrast agent is to be used and an operator may override the defaults when a different type is to be used. The next step 603 may be to retrieve one or more contrast agent type attributes. Such attributes may include contrast agent longitudinal and transverse relaxation times. The retrieval may be from a database in the memory 506 of the injection system 500, from an RFID tag associated with the contrast agent syringe 503, or from any other appropriate data storage device or combination of devices where attributes of a plurality of contrast agent types may be stored.

The next step 604 may be to input a cardiac output rate for the patient to be imaged. The cardiac output rate may be determined as described above. The next step 605 may be to input one or more imaging parameters that are to be used by the MRA imager 501 during the MRA imaging procedure. The next step 606 may be to select an equation that relates signal intensity to imaging parameters, contrast agent attributes and contrast agent concentration for the imaging sequence to be used by the MRA imager 501. For example, for a spin-echo imaging sequence, equation (3) above may be selected. Step 606 may be performed by the injection system 500 upon receipt of the imaging sequence type (e.g., inputted by the operator), or the specific equation may be selected by the operator. Alternatively, the injection system 500 may assume a default equation corresponding to a default imaging sequence type (e.g., spin-echo, gradient echo), and an operator may override the default sequence type when a different sequence type is to be used.

The next step 607 may be to determine a target in-bloodstream contrast agent concentration level. This step 607 may be performed by the target in-bloodstream contrast agent concentration determination module 508 which may calculate, using equation (3), a contrast agent concentration level where the rate of change of the signal intensity with respect to the concentration level equals zero using the obtained values for contrast agent type attributes and imaging parameters. Such a calculation determines the concentration level corresponding to the maximum signal intensity, and such a value may be used as the target in-bloodstream contrast agent concentration or a value offset from the concentration level corresponding to the maximum signal intensity may be used.

Once the target in-bloodstream contrast agent concentration is determined, the next step 608 may be to calculate a contrast agent injection rate using the contrast agent injection rate determination module 509. This calculation, using equation (5), may be based on the target in-bloodstream contrast agent concentration, the initial contrast agent concentration, and the cardiac output of the patient to be imaged. Once the contrast agent injection rate is determined and using the diluent injection rate determination module 510, the contrast agent injection rate may be subtracted from a standard total injection rate in step 609 to calculate the diluent injection rate.

Having determined the contrast agent injection rate and the diluent injection rate, the next step 610 may be to perform an injection using the injection system 500. Performing the injection may include inserting a catheter into a patient's vein, checking patency of the catheter, providing a contrast agent syringe 503 installed on the injection device 502, providing a diluent syringe 504 installed on the injection device 502, purging the injection system 500 of air, and any other typical injection preparation tasks. Once the injection system 500 is properly connected to the patient, the injection system 500 may discharge the contrast agent and diluent simultaneously at the contrast agent injection rate and the diluent injection rate, respectively (e.g. to achieve a desired total injection rate). In an embodiment, such discharging may not begin until after the target in-bloodstream contrast agent concentration level of step 607 has been determined. In an embodiment, such discharging may not begin until after the contrast injection rate of step 608 has been calculated. After an appropriate delay to allow the contrast agent to reach the patients heart, the MRA imager 501 may generate contrast agent enhanced images of the patient's vasculature.

Feedback from the signal intensity received by the MRA imager 501 may be used to control the contrast agent injection rate. In this regard, the contrast agent injection rate may be changed, adjusted or modulated using a closed-loop feedback system where MRA imager 501 data (e.g., signal intensity data and/or other appropriate data) is transferred from the MRA imager 501 to the injection system 500. Such a feedback system may be used to attain the target contrast agent concentration in the vasculature of the patient and/or achieve desired signal intensity. Such a closed-loop feedback system may be via a communication link between the injection system 500 and the MRA imager 501. Such a closed-loop feedback system may require an operator to either adjust the contrast agent injection rate in response to signal intensity or input signal intensity values from the MRA imager 501 into the operator interface 507.

When performing the method of operating an injection system 500 depicted in flow diagram 600, steps 601-607 may be performed in any appropriate order. For example, imaging parameters used during the MRA imaging procedure may generally be the same for a plurality of patients and may be programmed into the injection system 500 prior to an imaging session.

The above-described method may be repeated for a second patient. In the repeated performance of the method, a different contrast agent may be used and different contrast agent and diluent injection rates may be used. The same standard total injection rate may be used in both performances of the method.

The target in-bloodstream contrast agent concentration determination module 508, the contrast agent injection rate determination module 509 and the diluent injection rate determination module 510 may each be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. The target in-bloodstream contrast agent concentration determination module 508, the contrast agent injection rate determination module 509 and the diluent injection rate determination module 510 may each be implemented at any single location or at multiple locations that are interconnected in any appropriate manner (e.g., via any type of network).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A method for injecting a contrast agent into a patient to be imaged, comprising:
   receiving an indication of a first imaging parameter for a magnetic resonance angiography (MRA) imager to be used in an MRA imaging procedure;
   receiving an indication of a cardiac output rate of the patient to be imaged;
   receiving an indication of a type of contrast agent to be used in said MRA imaging procedure and an initial concentration of said contrast agent;
   determining a target concentration for a contrast agent in the bloodstream of the patient to be imaged, at least in part based on said type of contrast agent and said first imaging parameter;
   determining an injection rate for said contrast agent at least in part based on said target concentration, said initial concentration, and said cardiac output rate; and
   injecting said contrast agent at said injection rate into the patient.

2. The method of claim 1, wherein said determining of said target concentration further utilizes a second imaging parameter, wherein said first imaging parameter is a pulse repetition time for said MRA imager, and wherein said second imaging parameter is an imaging delay time for said MRA imager.

3. The method of claim 1, wherein said determining of said target concentration uses a formula relating contrast agent concentration in said patient to signal intensity received by said MRA imager during said MRA imaging procedure to determine a first level of concentration of said contrast agent where the rate at which the signal intensity changes divided by the rate at which the contrast agent concentration changes equals zero.

4. The method of claim 3, wherein said first level of concentration is used as said target concentration.

5. The method of claim 1, wherein said determining said injection rate includes dividing said target concentration by said initial contrast agent concentration to determine a concentration ratio and calculating said injection rate by multiplying said cardiac output rate by said concentration ratio.

6. The method of claim 1, further including determining a diluent injection rate at least partially based on said contrast agent injection rate.

7. The method of claim 6, wherein said determining said diluent injection rate includes subtracting said contrast agent injection rate from a standard total injection rate to determine said diluent injection rate.

8. The method of claim 1, wherein said first imaging parameter is one of a pulse repetition time for said MRA imager, an imaging delay time for said MRA imager, a signal intensity for said MRA imager, or a field strength for said MRA imager.

9. The method of claim 1, wherein said MRA imaging procedure is a spin-echo imaging sequence.

10. The method of claim 1, wherein said MRA imaging procedure is a gradient-echo imaging sequence.

11. The method of claim 1, further including providing an operator interface that receives inputs from an operator.

12. The method of claim 11, wherein said contrast agent type is received from said operator interface.

13. The method of claim 11, wherein said initial concentration of said contrast agent is received from said operator interface.

14. The method of claim 11, wherein said cardiac output rate is received from said operator interface.

15. The method of claim 11, wherein said first imaging parameter is received from said operator interface.

\* \* \* \* \*